United States Patent [19]
Mueller et al.

[11] Patent Number: 6,015,427
[45] Date of Patent: Jan. 18, 2000

[54] HEART STABILIZER WITH CONTROLLABLE STAY SUTURE AND CUTTING ELEMENT

[75] Inventors: Richard L. Mueller; Steve A. Daniel; Stuart D. Harman, all of Sunnyvale, Calif.

[73] Assignee: Eclipse Surgical Technologies, Inc., Sunnyvale, Calif.

[21] Appl. No.: 08/882,774

[22] Filed: Jul. 7, 1997

[51] Int. Cl.[7] .................................................... A61B 17/00
[52] U.S. Cl. .......................................... 606/232; 606/139
[58] Field of Search ................................... 606/232, 233, 606/1, 99, 148, 139, 150, 157, 158; 112/169, 80.03; 623/2; 600/508, 510

[56] References Cited

U.S. PATENT DOCUMENTS

| | | | |
|---|---|---|---|
| 3,831,608 | 8/1974 | Kletschka et al. | 606/232 |
| 3,857,396 | 12/1974 | Hardwick | 606/232 |
| 3,874,388 | 4/1975 | King et al. | 606/233 X |
| 4,016,883 | 4/1977 | Wright, Jr. | 606/232 X |
| 4,667,675 | 5/1987 | Davis | 606/232 |
| 5,127,412 | 7/1992 | Cosmetto et al. | 606/232 |
| 5,730,757 | 3/1998 | Benetti et al. | 606/198 |

*Primary Examiner*—Michael Buiz
*Assistant Examiner*—Vikki Trinh
*Attorney, Agent, or Firm*—Ray K. Shahani; Janet Kaiser Castaneda

[57] ABSTRACT

A heart stabilizer and suture control device for stabilizing the heart and for occluding a preselected portion of coronary artery by developing a downward force on the heart and simultaneously developing an upward force across a coronary artery in a predetermined position. The device has at least two stabilization pads, the stabilization pads each having an operative size and shape, and each having a first end and a second end and a lower contacting surface. The second ends have suture retaining grooves, and the stabilization pad has a suture locking means for securing the distal end of a suture means thereto. The device also comprises a linking member locking the two stabilization pads an operative distance apart. The device has suture means with a proximal end coupled to the linking member and extending from the first end to the suture retaining groove of the second end, the suture means having a distal end which can be locked to the stabilization pad with the suture locking means thereon. The device also has means for rotating the linking member such that when operatively positioned adjacent a coronary artery to be occluded with the suture threaded between the coronary artery and the remaining portion of the heart muscle, rotating the linking member will cause the proximal end of the suture means to be wound onto the linking member and thus tighten the suture between the first end and the second end of each stabilization pad and urge the coronary artery against the contacting surface, thereby causing occlusion of the coronary artery as desired.

33 Claims, 14 Drawing Sheets

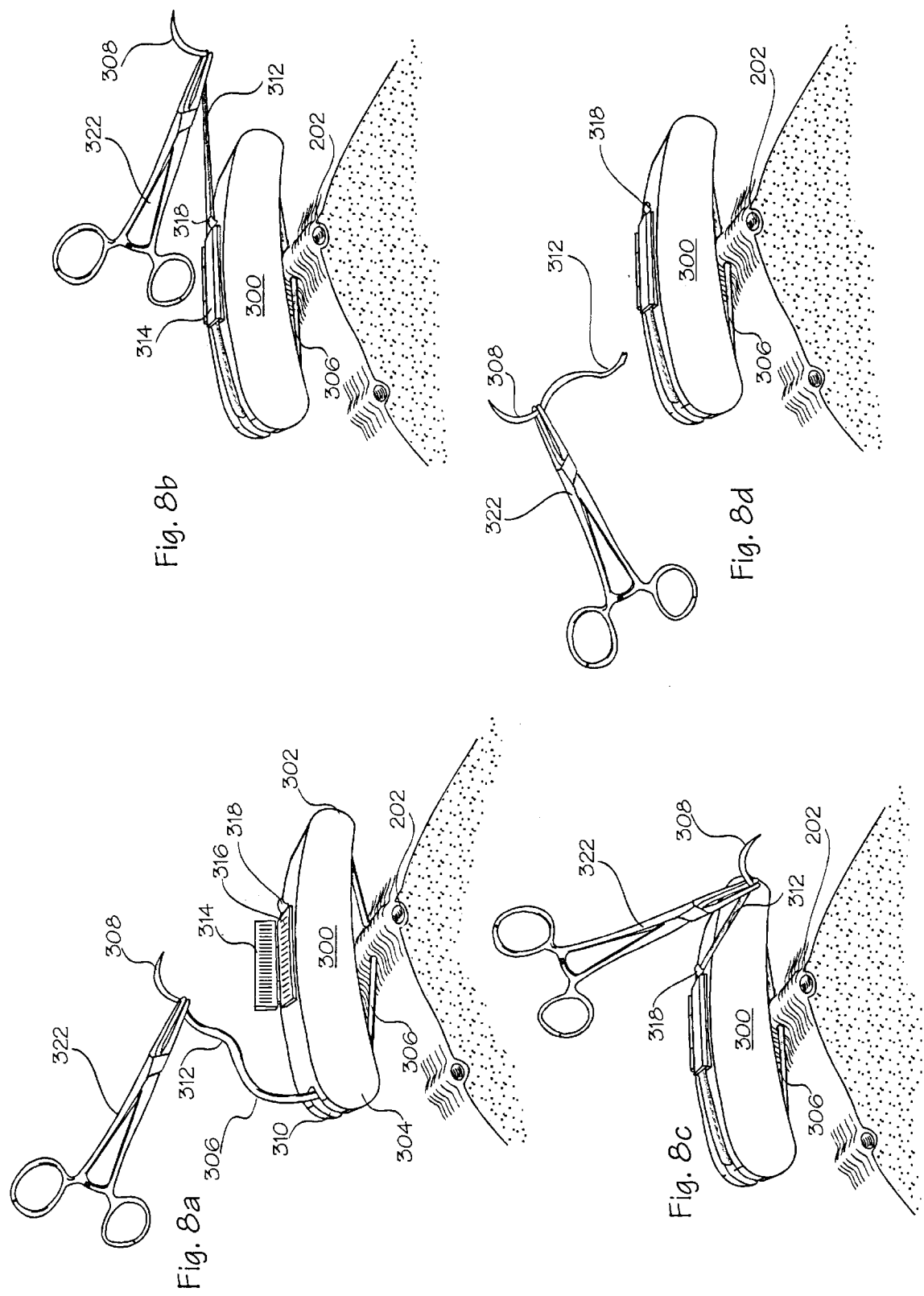

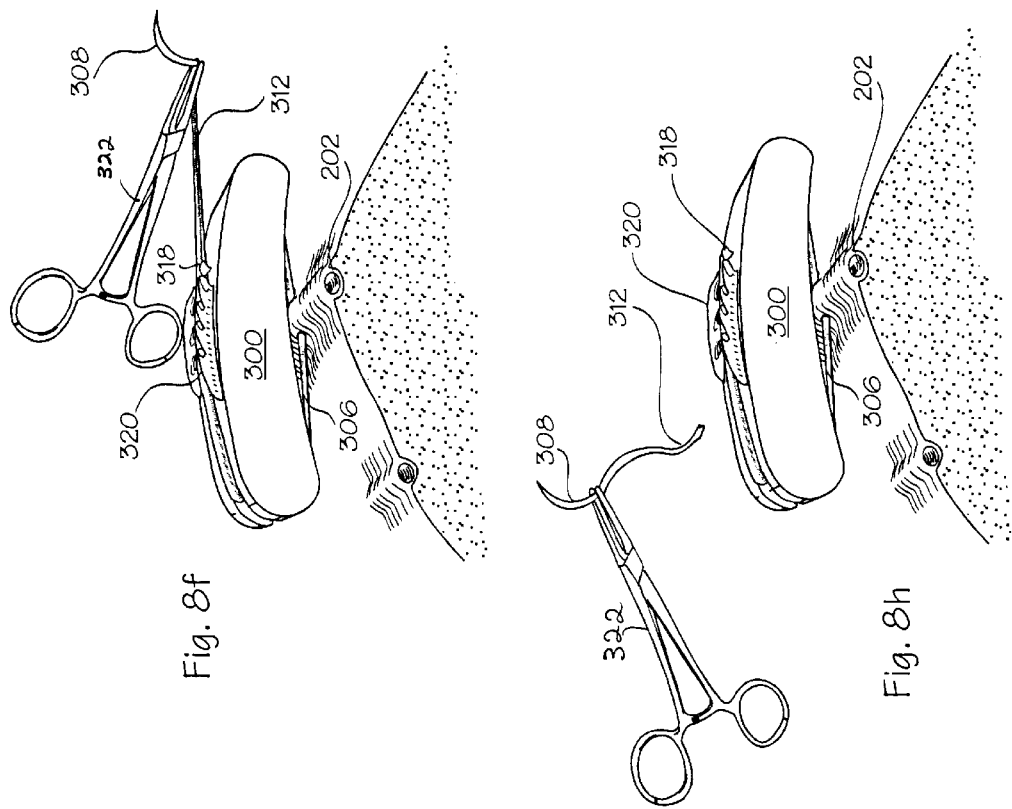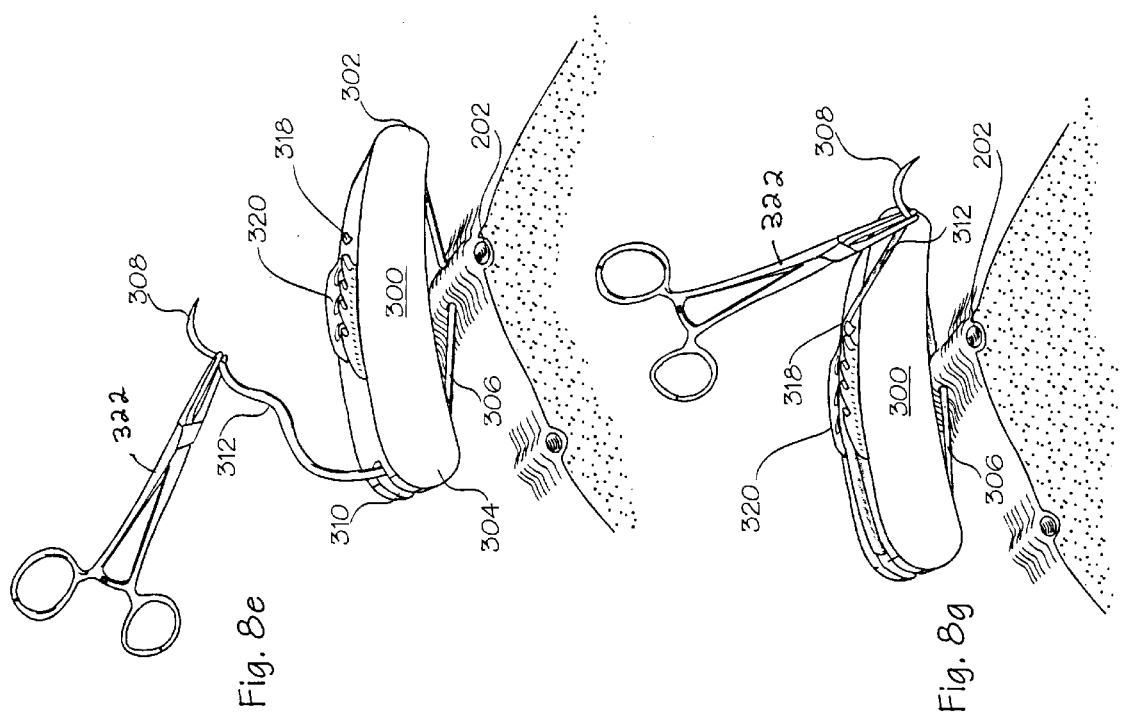

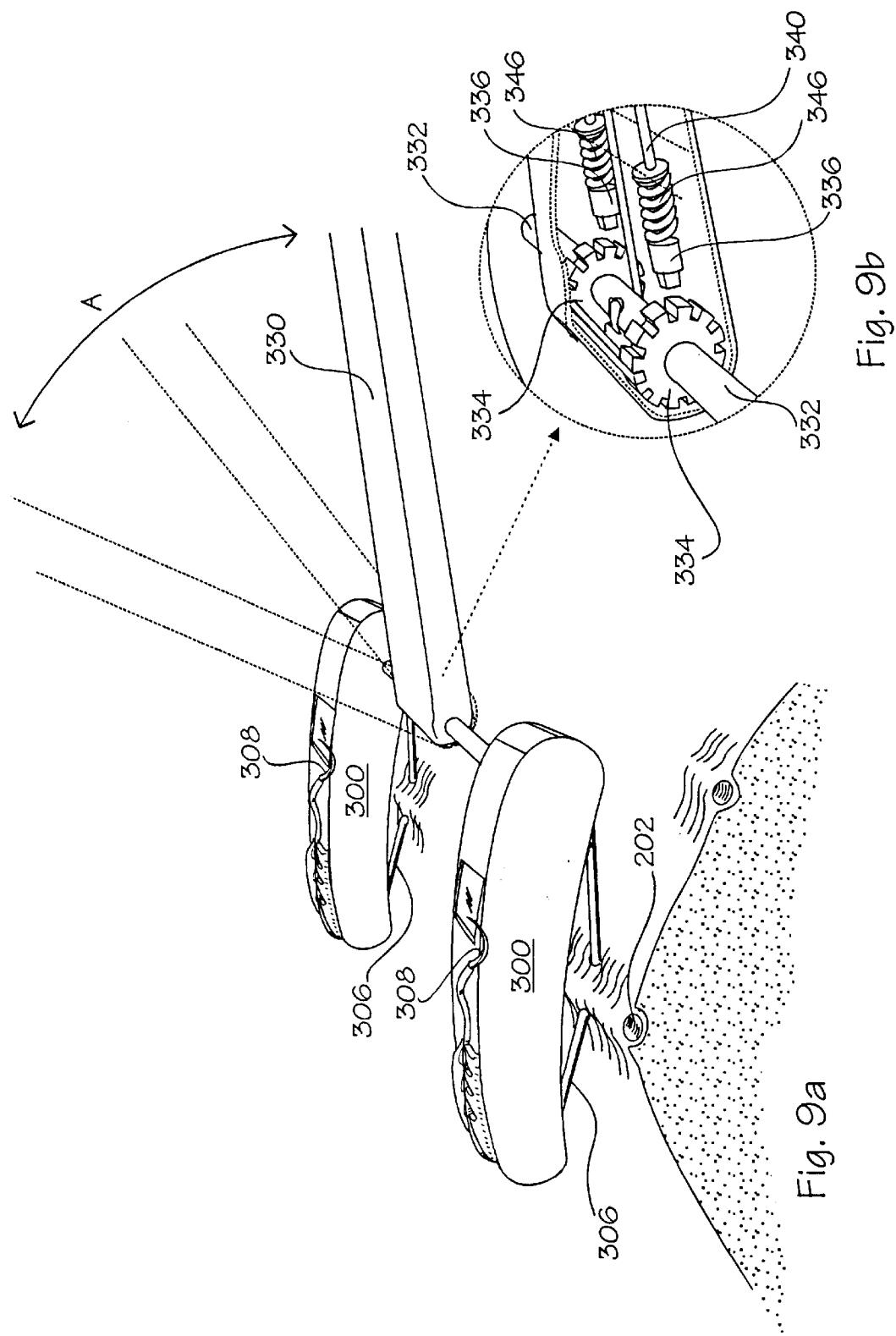

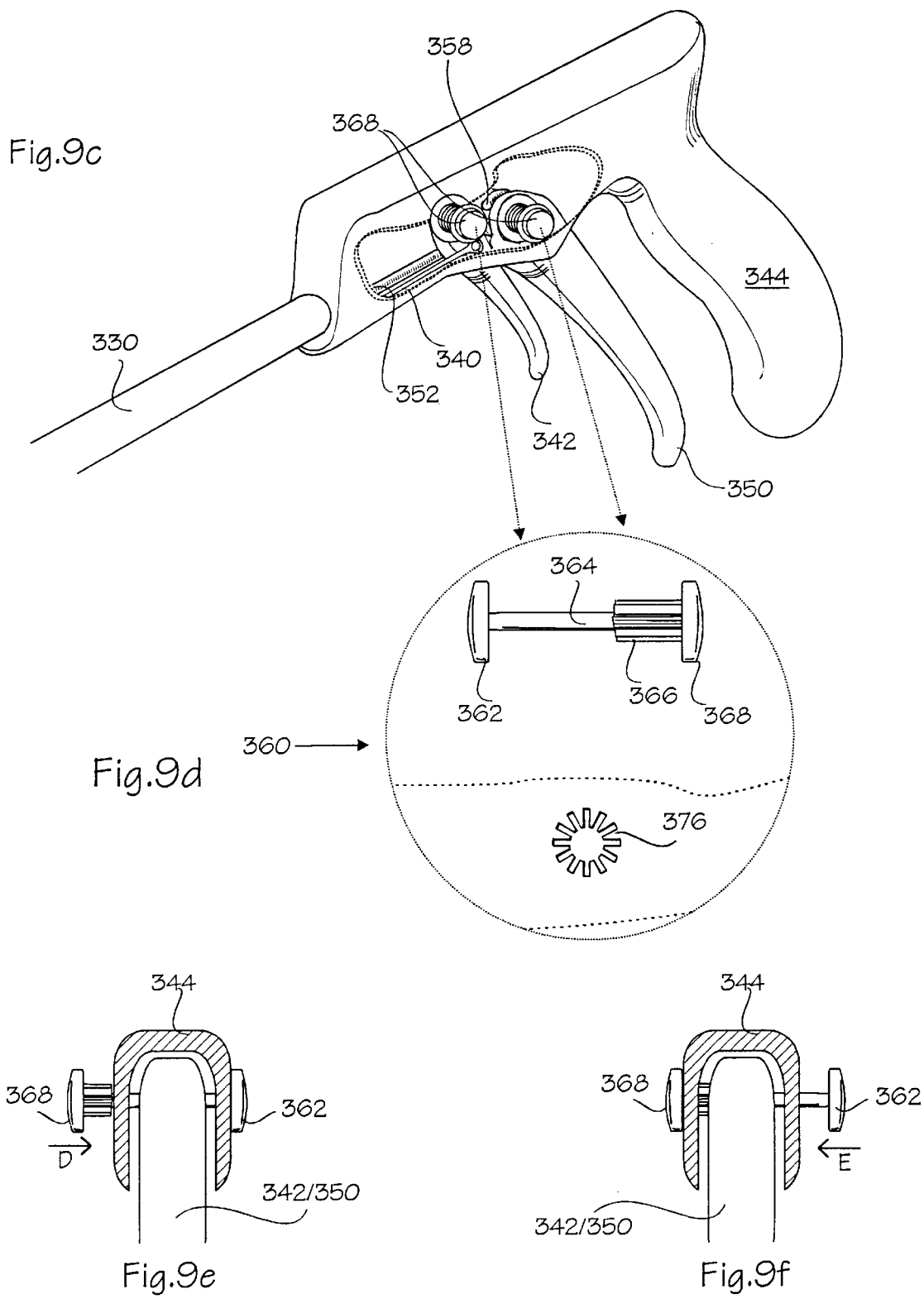

HEART STABILIZER WITH CONTROLLABLE STAY SUTURE AND CUTTING ELEMENT

FIELD OF THE INVENTION

The present invention relates generally to apparatus and methods for minimally invasive cardiovascular surgical procedures and more particularly to apparatus and methods of stabilizing and immobilizing the heart for anastomosis of blood vessels to the coronary arteries, using devices to develop compressive forces in the heart, such as in transmyocardial revascularization (TMR) enhanced minimally invasive direct coronary artery bypass (MIDCAB) or any other similar MIS procedures.

BACKGROUND OF THE INVENTION

Coronary Artery Disease

Heart disorders are a leading cause of death in developed countries. Such disorders also impair the quality of life of millions of people by restricting activity because of pain, breathlessness, fatigue, fainting spells and anxiety. The major cause of heart disease in developed countries is impaired blood supply. One cause of reduced blood supply to the heart is coronary artery disease.

FIG. 1 is a schematic view of the coronary arteries on the outer surface of the human heart. Though the heart supplies blood to all other parts of the body, the heart itself has relatively little communication with the oxygenated blood supply. Thus, the coronary arteries essentially comprised of the right anterior descending (RAD) coronary artery 100, the left anterior descending (LAD) coronary artery 102 and the circumflex (CIR) coronary artery 103 arise from the aorta 104 beneath the aortic arch 106. The coronary arteries encircle the heart muscle on either side "like a crown" to supply the heart muscle itself with blood.

Coronary artery disease generally involves and results in a narrowing of the coronary arteries due to atherosclerosis. The resulting ischemia or blockage can lead to angina pectoris, a pain in the chest, shoulders, arms or jaw due to a lack of oxygen to the heart, or infarction, death of an area of the myocardium caused by the ischemia.

Coronary artery blockage can be relieved in a number of ways, including drug therapy, utilization of nitrates, beta-blockers, and peripheral vasodilatator drugs (to dilate the arteries) and thrombolytic drugs (to dissolve the clot). Transluminal angioplasty is often indicated—the narrowed part of the artery, clogged with atherosclerotic plaque or other deposits, can be stretched apart by passing a balloon to the site and gently inflating it a certain degree. Additionally, stents or other tubular structures can be implanted during angioplasty to hold the walls of a vessel apart. Risks attendant with angioplasty include blockage of the coronary arteries essentially completely during the time the balloon is being placed and expanded, and also the possibility that portions of the atherosclerotic material can become dislodged which may cause a total blockage at a point downstream of the subject occlusion thereby requiring emergency procedures.

CABG and MIDCAB

Coronary artery bypass grafting (CABG) is a procedure in which the coronary arteries are bypassed for delivering oxygenated blood to myocardium. CABG is the most common and successful major heart operation performed with over 500,000 procedures being performed annually in the United States alone. CABG may be performed as a sternotomy procedure, or more recently, as a MIDCAB procedure (see below). In a sternotomy, a cardiac surgeon makes a sternotomy incision down the center of the patient's chest and the heart is exposed by opening the pericardium. A length of vein is removed from another part of the body, typically the leg. The patient is connected to a heart-lung machine which takes over the function of the heart and lungs during the operation. The section of vein is first sewn to the aorta and then sewn onto a coronary artery at a place such that oxygenated blood can flow directly into the heart. Not only does the procedure typically require the installation of the heart-lung machine but the sternum must be sawed through and the risk of infection is enhanced during the time the chest cavity is spread open.

The use of the cardiopulmonary bypass (CPB) machine has become standard for CABG and other procedures because the beating heart can typically tolerate only about one minute of blood flow interruption before the distal anatomy of the heart reacts to the lack of oxygenated blood and the risk of heart ischemia or infarction increases. The CPB machine takes over the heart's function of pumping oxygenated blood through the rest of the body during surgical intervention, typically 20 minutes up to several hours in duration.

Minimally invasive surgical (MIS) procedures have recently become popular due to the availability of sophisticated materials of construction and smaller designs of surgical and visualization equipment. Minimally invasive direct coronary artery bypass (MIDCAB) is an alternate way to revascularize the coronary vessels using arterial conduits without extracorporeal circulation. *Video Assisted Coronary Bypass Surgery* by Benetti, et al., J. Card. Surg., 10:620–625 (1995). Various apparatus are recently available for performing such MIS procedures.

FIG. 2 is a representative drawing showing typical locations of sternotomy and thoracotomy incisions. It will be understood that the present invention includes use of these and other incision locations. The MIDCAB procedure replaces the traditional, "open-heart" traumatic vertical sternotomy incision 160, in which the entire chest cavity is opened, with a shorter, more horizontal thoracotomy incision 162 to work on the still beating heart. Typically, no CPB equipment is needed. The thoracotomy exposes the heart over the fifth left intercostal space, or elsewhere as desired by the cardiac surgeon. Using a thorascope in the thorax to enhance visualization via video signal, a portion of the left internal mammary artery (LIMA) is harvested and grafted directly to the left anterior descending (LAD) coronary artery 102. The same procedure can be performed on the right side using the RIMA and the RAD 100, in the center for treating blockages of the circumflex coronary artery 103, or otherwise.

In most CABG or MIDCAB procedures, however, either before or at the time an incision is made in the coronary artery itself, blood flow through the coronary artery must be arrested using pressure, suction or a silastic band or clamp, or by placing stay sutures proximal to the bypass site and tightening the sutures to provide a dry field. Placement of these stay sutures is not always a simple matter, since as the heart is beating vigorously movement of the entire heart muscle makes precise placement of such stay sutures difficult.

FIGS. 3A and 3B are representative perspective views showing alignment of a portion of a vessel for CABG with an incision in the coronary artery, and the attached portion sewn into place onto the coronary artery, respectively. As described, during the typical CAB procedure, a vessel graft 200 is harvested from another portion of the vasculature. The proximal end, not shown, can be attached directly to the aorta, or the vessel to be grafted to the coronary artery 202 can be a segment of a nearby artery like the LIMA or the RIMA. The LIMA or RIMA can be severed at only one point somewhat distal from the uppermost portion of the LIMA where it originates adjacent the aorta, and grafted directly to the coronary artery at a point distal to the stenosis or other occlusion.

Various conventional methods are used for temporarily blocking blood flow through the coronary artery for performing CABG or MIDCAB. It will be understood that unless the coronary artery is completely blocked, blood will flow out of the coronary artery 202 at the point of the incision 204. For this reason, before the vessel graft 200 can be sutured into place, a section of the coronary artery 202 must be occluded. This can be done in a number of ways. In a simple method, the coronary artery 202 can be occluded by exerting pressure across the coronary artery 202 with a blunt instrument 210. Alternatively, a suction tube (not shown) can be operatively positioned adjacent the incision 204 in the coronary artery 202 to eliminate excessive blood loss in the operative field using a vacuum (also not shown). Once a portion of vessel graft 200 is made available, an incision 204 is made directly in the coronary artery 202 at a point distal to the stenosis or other occlusion. The distal end 206 of the vessel graft 200 is sutured 208 directly to the coronary artery 202 so as to provide communication of oxygenated blood through the vessel graft 200 into the coronary artery 202 directly.

FIG. 4 is a representative perspective view of the double stay suture method of occluding the coronary artery. As shown, a third solution is to clamp the coronary artery with one or more stay sutures, such as silastic bands 214 or other suitable clamps. After the anastomosis is created, the stay sutures 214 can be removed. Additionally, the stay sutures may be releasable and re-tightenable. This gives the cardiac surgeon the ability to occlude the vessel, attach the anastomosis, and release the stay sutures in order to determine the integrity of the anastomosis. In the event said anastomosis is inefficiently attached, poorly placed, leaks blood, etc., the stay sutures can be re-tightened and additional stitching or attachment of the vessel graft to the coronary artery can be achieved.

Cardiovascular Systems of Allen, Texas manufactures at least one type of elastic stay suture which is designed to occlude the coronary artery in a less traumatic manner. These stay sutures are formed of silastic tubing, filled with air or other fluid, and sealed at each end. By using this type of stay suture, less trauma is caused to the coronary arteries by virtue of its larger diameter and elastic/soft surface with cushion of air which distributes the occluding forces developed over a larger area.

Various devices have been described for assisting the cardiac surgeon attach the vessel graft to the coronary artery. United States Surgical Corporation (USSC) has recently announced a "Mini-CABG Access Set". *USSC Cardiovascular Marketing Newsletter,* Vol. I, Number 1, November, 1996. The newsletter describes the "VCS Clip Applier" which applies a non-penetrating titanium clip to the everted edges of co-apposed vessels. The apparatus is used to perform vascular anastomosis in AV fistulas, femoral bypasses, organ transplants, pediatric surgery as well as coronary artery bypass procedures.

U.S. Pat. Nos. 5,389,102 issued Feb. 14, 1995 and 5,573,541 issued Nov. 12, 1996, both to Green et al. teach apparatus and methods for subcuticular stapling of body tissue. These patents teach hand-held devices with pistol-type grips with members which grasp the edges of two body tissue portions to be connected together. As the spring-loaded apparatus is manually actuated, rod-like fasteners are moved into position to clamp or staple the two body tissue portions together.

U.S. Pat. No. 5,490,856 issued Feb. 13, 1996 to Person et al. teaches a purse string stapler. The apparatus includes scissors-type handles and a stapling assembly for emplacing a suture and staples into tissue as a purse string suture.

Unfortunately, the prior art is does not solve the problem of immobilizing the heart during placement of stay sutures prior to forming the anastomosis. Prior to the advent of MIS technology, stabilization of the heart muscle was often accomplished with an assistant, manually holding the heart muscle from underneath with one hand, while the cardiac surgeon formed the anastomosis.

FIG. 5 is a representative perspective view of a fork-type stabilizer 220 mounted on an MIS sternotomy collar 222. With MIS, use of a fork-type stabilizer 220 is prevalent, either held in place by an assistant, clamped separately to the operating table or other stationary object, or otherwise fixed in place relative to the chest cavity of the patient (as shown). The device has at least two tines 224 which are placed transverse to a selected portion of LAD or other portion of coronary artery 202. By pivoting the device about its point of attachment 226 on handle portion 228, the tines 224 Will press across the coronary artery and block any (at least as much as desired) blood flow therethrough. Furthermore, releasing the pressure from the fork stabilizer 220 will allow continued movement of the heart, resulting in loss of original position of the fork stabilizer 220 on the coronary artery.

FIG. 6 is a representative perspective view of a "bull dog"-type clamp 230 commonly used to occlude vessels in cardiac surgery. The clamp 230 has a pair of adjustably positionable soft jaws 232 which clamp gently across a vessel as desired. Drawbacks to this type of clamp 230 include the need to manipulate a small nut-type head to release the occluding force across the coronary artery 202. Additionally, the clamp alone, unless associated with other structure, cannot provide sufficient stabilizing effect on the heart muscle. Without the stabilizing effect of the present invention, the task of suturing an anastomosis to a coronary artery is quite a bit more difficult.

FIG. 7 is a representative perspective view of a stabilizing fork device 240 associated with a ring base-type sternotomy collar 242. The USSC newsletter mentioned above also describes the "Universal Ring Base", an oval-shaped platform which offers 360° access to the surgical site. The apparatus comes fitted with a range of positionable retractors and a gear-toothed profile around the extremity of the ring base for positioning the retractors as well as suture organizing equipment in a non-slipping configuration. A similar approach to MIDCAB is disclosed by Cardio Thoracic Systems (CTS). An access platform apparatus, similar at least in function to the ring base by USSC, provides limited access and certain visualization capability to the cardiac surgeon.

The stabilizing collar 242 clamps into place with clamp means 244 within the thoracotomy incision with a pair of adjustable, locking spreading arms 246 which, typically, would lift and spread the ribs apart providing access to the beating heart. The apparatus provides a platform for securing a conventional fork-type stabilizer 240 in place. As described above, the rigid tines of the fork-type stabilizer 240 are placed directly on top of a coronary artery to occlude a portion of the coronary artery therebetween, in order to effect anastomosis of the vessel between or adjacent the times.

A simple "hemostat"-type clamp which is designed for atraumatic occlusion is described by U.S. Pat. No. 4,821,719 issued Apr. 18, 1989 to Fogarty. This clamp, however, is much less desirable than a simple stay suture since it is considerably larger than a suture and therefore needs to be supported somehow. Additionally, once released, the clamp will need to be repositioned, thus taking additional operating room time and increasing the overhead cost of the procedure.

One problem with the prior art, therefore, is that none of the described devices are particularly suited to place an occlusion such as a stay suture, perform some procedure on the occluded vessel, allow removal of the blockage, and then permit re-blocking the vessel in order to alter the anastomosis somehow or for some other reason. Another drawback of the prior art is that when conventional stay sutures are used, the angle at which they pull across the coronary artery often causes trauma to the artery.

As is evident by a review of the prior art, the stay suture method lifts the heart for immobilizations and the fork type devices all tend to develop a downward force on the heart. In a typical open-heart surgery, the heart is supported by the hands of the cardiac surgeon or an assistant from underneath. Both of these support modes are helpful, but there is no single device which will achieve both. It would be very desirable, therefore, to provide an apparatus and method to temporarily occlude the coronary artery precisely where desired. It would also be desirable to provide a device and method for compressing, supporting and immobilizing the heart, for occluding a blood vessel and simultaneously applying a releasable stay suture.

ADVANTAGES AND SUMMARY OF THE INVENTION

Thus, it is an advantage of the present invention to provide a method and apparatus for performing CABG or MIDCAB heart surgery on a beating heart which overcome the disadvantages of the prior art.

It is also an advantage of the present invention to provide an apparatus and method to apply and develop compressive, supportive and stabilizing forces on the heart.

It is a further advantage to provide a device and method for immobilizing the heart, for occluding a blood vessel, including vessels attached to surrounding tissue, whether native or explanted, and vessels which are not attached to surrounding tissue, whether native or explanted, and simultaneously applying a releasable stay suture.

Therefore, in summary, the present invention is a stabilization pad for immobilizing the heart while simultaneously placing a stay suture around a coronary artery. The device develops a downward force on the heart and simultaneously develops an upward force across a coronary artery in a predetermined position. The device has a clamping mechanism to avoid manually tying the suture in place. A releasable tightening mechanism allows the suture to be tightened into place and released when desired, maintaining the position of the suture for any necessary re-tightening at a later point in time.

In a preferred embodiment, the device has a manually operated ratchet mechanism for efficiently effecting the tightening and release function.

In a preferred embodiment, two or more individual stabilization pad portions are coupled together for immobilizing the heart and for placing two or more stay sutures around a coronary artery, for manually tightening the two or more stay sutures in place either one at a time or at the same time, and for releasing the tension on the two or more stay sutures either one at a time or simultaneously.

Numerous other advantages and features of the present invention will become readily apparent from the following detailed description of the invention and the embodiments thereof, from the claims and from the accompanying drawings.

BRIEF DESCRIPTION OF THE DRAWINGS

FIGS. 8a–8d show a preferred embodiment of the stabilization pad suture controller of the present invention in prior and subsequent steps, respectively, of the method of the present invention.

FIGS. 8e–8h show an additional preferred embodiment of the stabilization pad suture controller in initial and subsequent steps, respectively, of the method of the present invention.

FIGS. 9a and 9b show, respectively, representative perspective and detail views of the rotating extension portion coupled to two stabilization pad suture controllers of the present invention and a detail of the pivot linkage.

FIGS. 9c–9f show representative perspective, detail and partial section views of the handle portion of the present invention.

DETAILED DESCRIPTION OF THE PREFERRED EMBODIMENT

Figure 1:
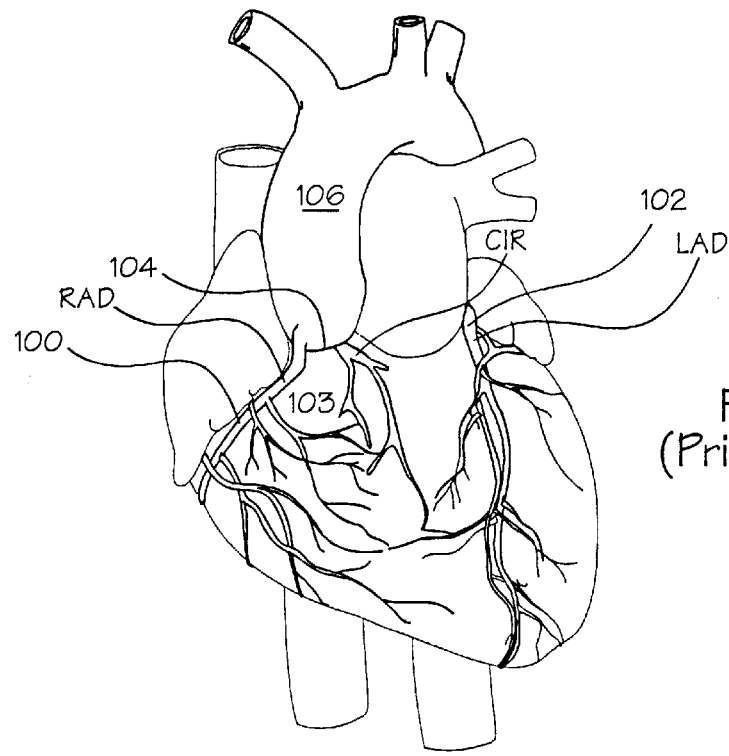
FIG. 1 is a schematic view of the coronary arteries on the outer surface of the human heart.
Figure 2:
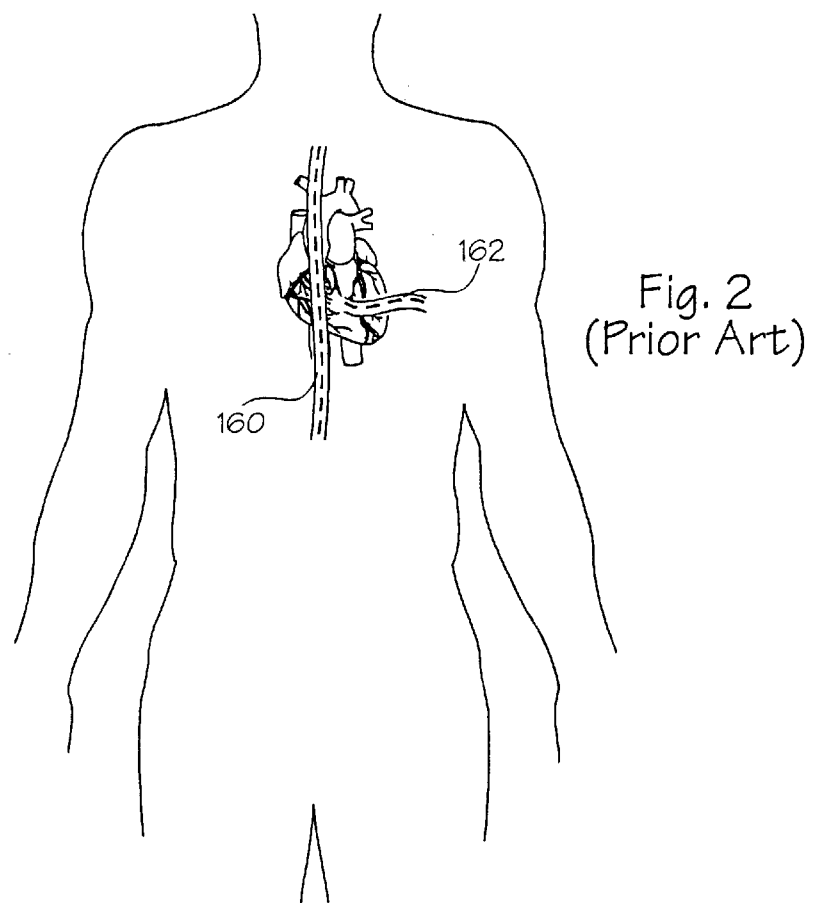
FIG. 2 is a representative drawing showing typical locations of sternotomy and thoracotomy incisions.
Figure 3A:
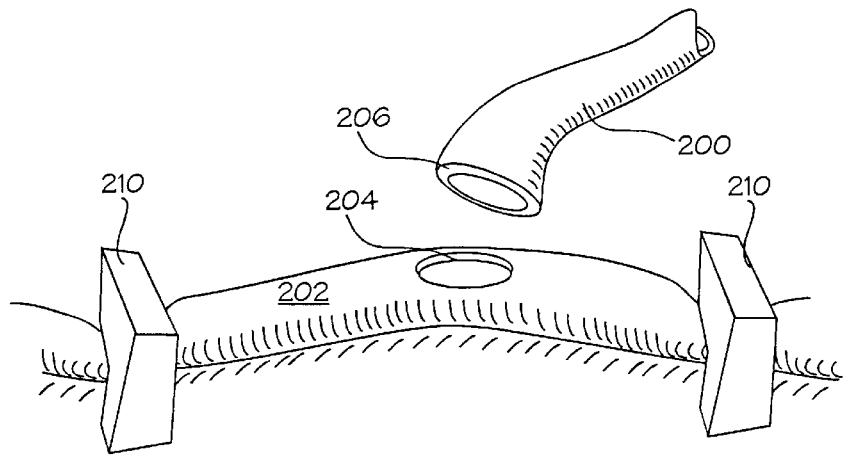
FIGS. 3A and 3B are representative perspective views showing alignment of a portion of a vessel for CABG with an incision in the coronary artery, and the attached portion sewn into place onto the coronary artery, respectively.
Figure 3B:
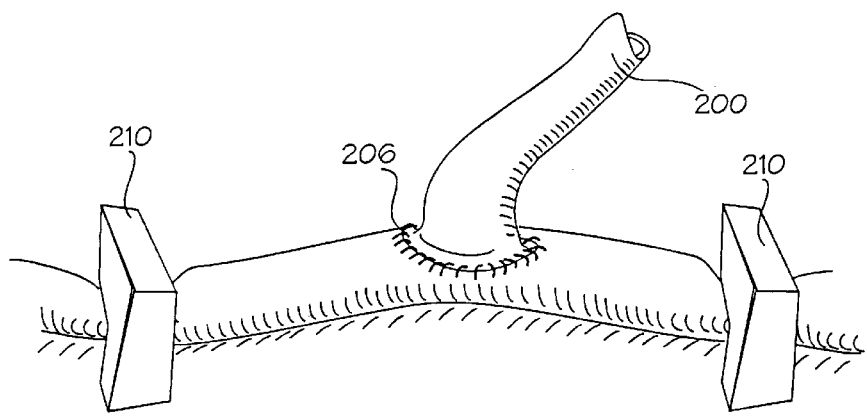
Figure 4:
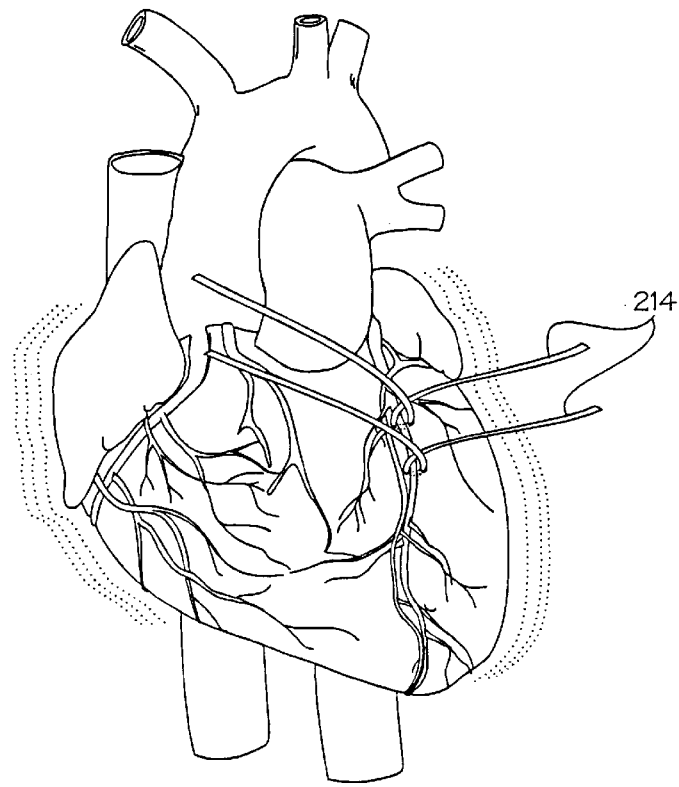
FIG. 4 is a representative perspective view of the double stay suture method of occluding the coronary artery.
Figure 5:
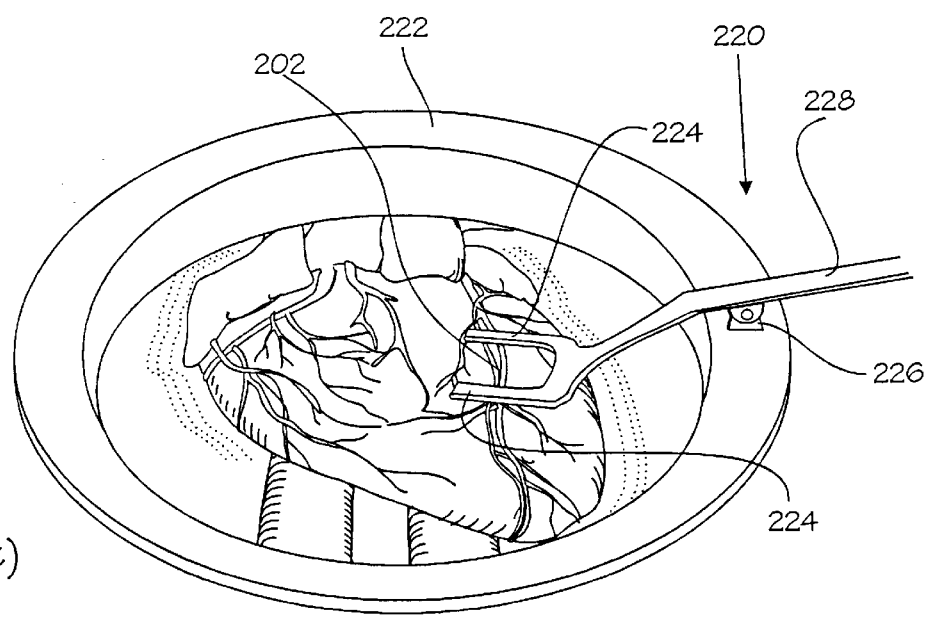
FIG. 5 is a representative perspective view of a fork-type stabilizer mounted on an MIS sternotomy collar.
Figure 6:
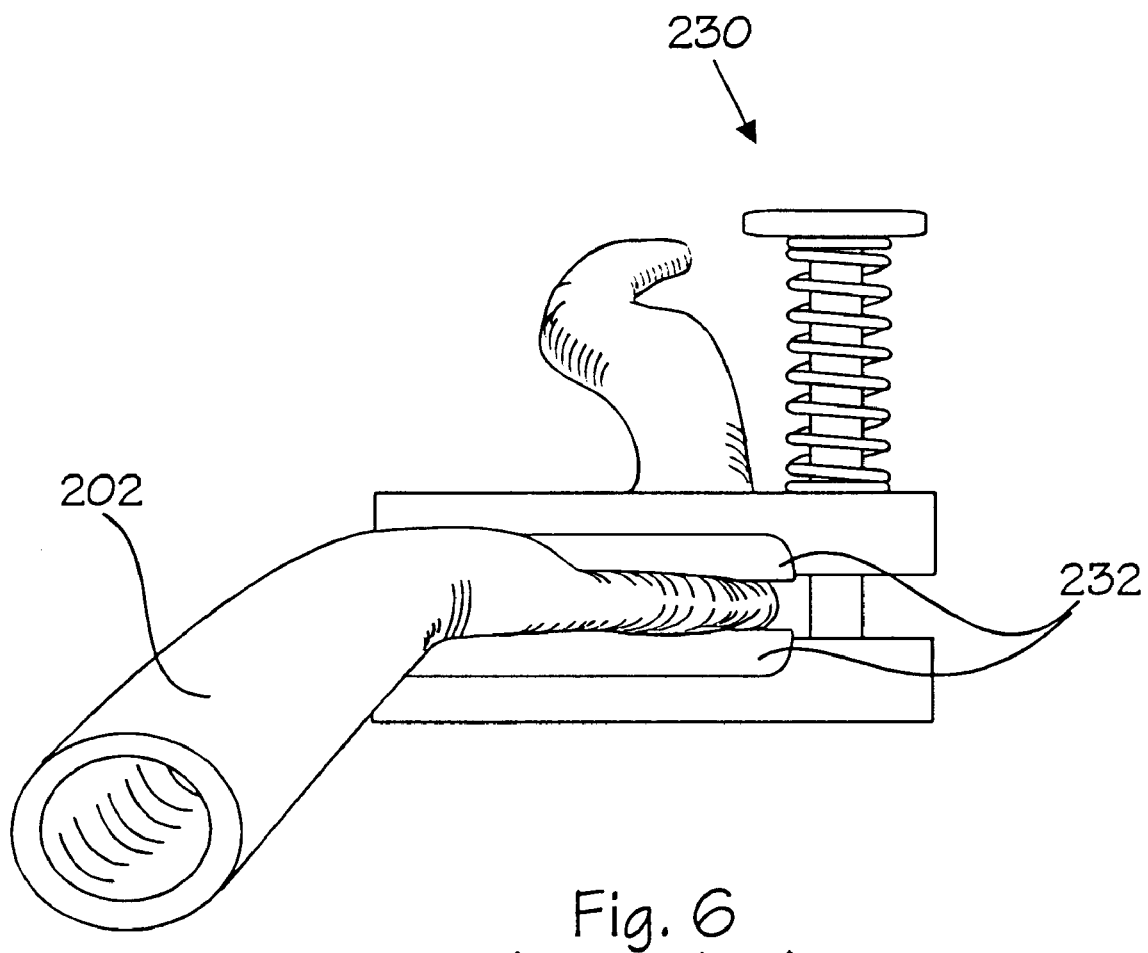
FIG. 6 is a representative perspective view of a "bull dog"-type clamp commonly used in cardiac surgery.
Figure 7:
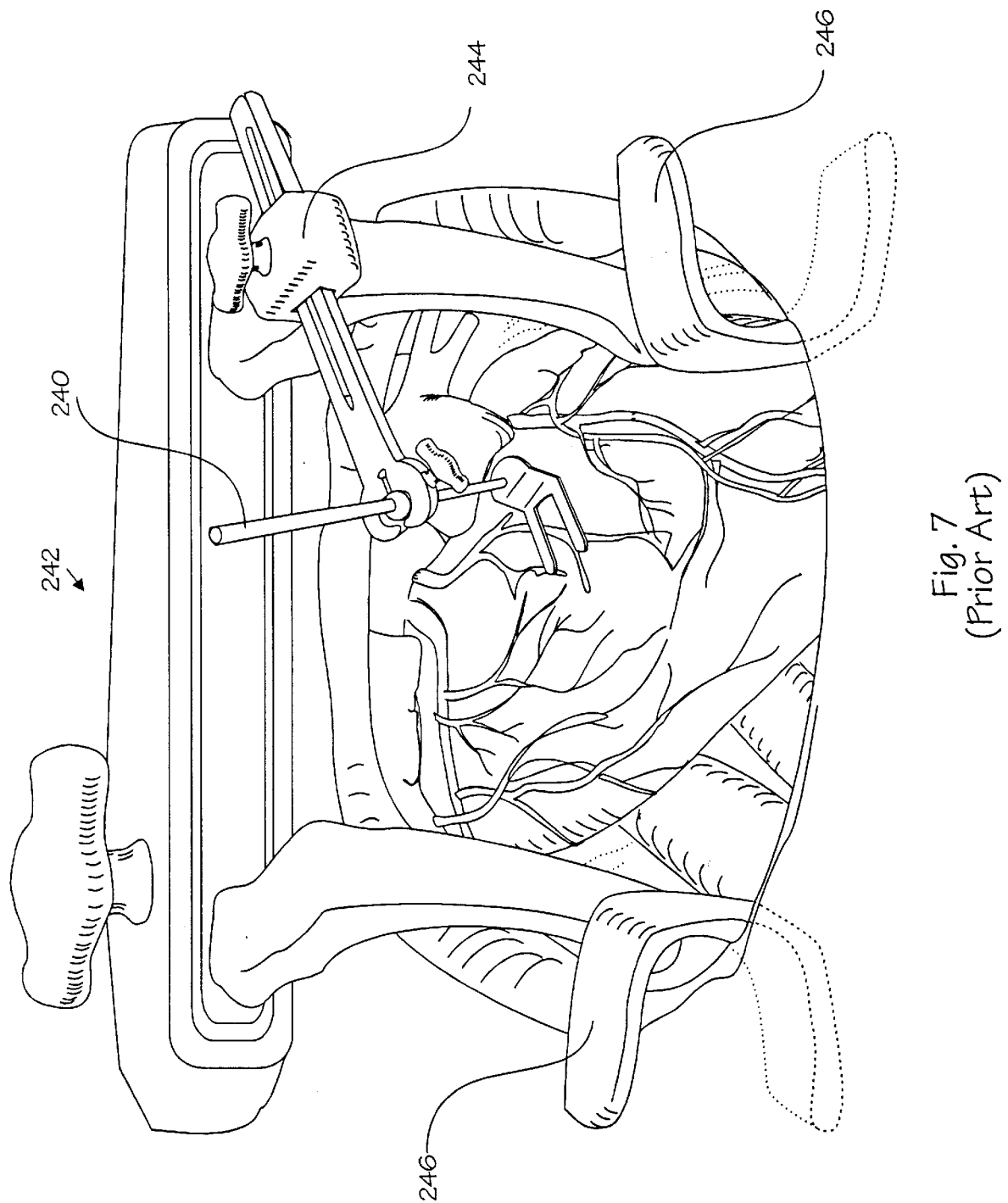
FIG. 7 is a representative perspective view of a stabilizing fork device associated with a ring base-type sternotomy collar.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function will have like reference numerals associated therewith.

FIGS. 8a–8d show a preferred embodiment of the stabilization pad suture controller of the present invention in prior and subsequent steps, respectively, of the method of the present invention. The stabilizer pad 300 has a first end 302 and a second end 304. The suture 306 initiates within the first end 302 and is threaded underneath the coronary artery by means of a piercing tip 308. The suture is threaded through a guide groove 310 at the second end 304 of the stabilization pad 300. As shown, this procedure would generally be accomplished using a conventional or other pair of hemostat clamps 322. As shown in FIG. 8b, the distal end 312 of suture 306 can be drawn in a forward direction and placed between locking door 314 on live hinge 316. In this manner, the distal end 312 of suture 306 will be held in place while the suture 306 is tightened from the suture control portion of the device.

Another advantage of the present invention, as shown in the drawings, is that tightening forces which occlude the vessels are developed at the ends 302 and 304 of the stabilizer pad 300, thereby preventing upward forces exerted directly on the coronary artery 302. As described below especially with regard to FIGS. 11a–11c, a cushioned, textured and/or grooved tissue contacting surface on the stabilizer pad 300 will add to the occluding efficiency of the invention.

Then, as shown in FIGS. 8c and 8d, drawing the suture 306 to one side across a small cutting element 318, similar to that found on a container of dental floss, will result in severing the piercing tip 308 from the distal end 312 of the suture 306. The small cutting element 318 is optional, but in the small confines of a mini thoracotomy incision and operating field, the convenience of such will be evident to those skilled in the art. Said cutting element 318 can have any of various configurations, but a low profile will be advantageous. In this configuration, the stay suture 306 of the stabilization pad 300 can be conveniently threaded under the coronary artery and locked in place, for further manipulation as desired.

The invention is a device and method for immobilizing the heart, for occluding a blood vessel, including vessels attached to surrounding tissue, whether native or explanted, and vessels which are not attached to surrounding tissue, whether native or explanted, and simultaneously applying a releasable stay suture thereto.

FIGS. 8e–8h show an additional preferred embodiment of the stabilization pad suture controller in initial and subsequent steps, respectively, of the method of the present invention. As in the prior drawings, the stabilizer pad 300 has a first end 302 and a second end 304. The suture 306 initiates within the first end 302 and is threaded underneath the coronary artery by means of a piercing tip 308. The suture is threaded through a guide groove 310 at the second end of the pad 300. Hemostat or other clamp means 322 will be useful in drawing the stay suture forward, as shown in FIG. 8f, between opposing jam members of jam cleat 320. In this manner, the distal end 312 of suture 306 will be held in place within jam cleat 320 while the suture 306 is tightened from the suture control portion of the device. It will be understood that the jam cleat 320 is constructed similarly to the essentially one-way, line-locking devices found on marine vessels such as sailboats, etc. Opposing jam members extend from the central portion of a line catching groove in a forward direction, and when the line is laid in place within the groove and drawn in a backwards direction, the jam members cause the flexible material of the line to deform slightly and "jam" within the cleat, thereby preventing movement in a backwards direction. Typically lines can be released from such jam cleats by tugging slightly in a forward and upward direction to lift the line from the groove.

Thereafter, as in the prior embodiment and as shown in FIG. 8g, distal end 312 of stay suture 306 can be drawn to one side across a cutting element 318. This will conveniently and easily sever piercing tip 308 and distal end 312 of stay suture 306 from the stabilization pad 300, leaving the stay suture 306 locked in place under coronary artery 202 and within jam cleat 320.

FIGS. 9a and 9b show, respectively, representative perspective and detail views of the rotating extension portion 330 coupled to two stabilization pads 300 of the present invention and a detail of the pivot linkage. Extension portion 330 pivots about linking member 332 by means of a toothed gear or gears 334 attached to linking member 332. Extension member 330 also houses locking pins 336 such that when the pins 336 are retracted, as shown, the extension portion 330 is able to pivot upwards and downwards, in, directions A, and when the pins are extended to engage toothed gear or gears 334, the extension portion is locked in a given position. Locking pins 336 are controlled by an anti-rotation mechanism including rotation control lever 342 as will be described below, especially in connection with FIG. 9c. Utilizing this design, the angle formed between the stabilization pads 300 and the supporting mechanism can be adjusted so as to be most effective at stabilizing a portion of the coronary artery and the heart muscle and to obtain optimum field of view for performing the procedure. Not only can extension shaft 330 be moved in a downwards direction to provide visual clearance within the operating field, but the extension shaft 330 can also be lifted or pushy in the locked position so as to provide sufficient downward, compressive forces, or upward support forces, on the beating heart for stabilization thereof.

FIGS. 9c–9f show representative perspective, detail and partial section views of the proximal handle portion of the present invention. One or more anti-rotation locking pin shafts 340 extend distally from handle 344 and terminate in locking pins 336 (FIG. 9b). The pivoting rotation mechanism is controlled by rotation control lever 342 mounted in handle portion 344. In a preferred embodiment, the shaft or shafts 340 can be spring loaded such as with springs 346, such that manual or other activation of rotation control lever 342 will retract the heads of locking pins 336 from engagement with the toothed gear or gears 334, thus permitting rotation of extension portion 330 as desired. Upon determination of an optimum angle between extension portion 330 and stabilization pads 300, the rotation control lever 342 can be released allowing spring or springs 346 to cause pins 336 to engage toothed gears 334 and prevent any undesired rotation of extension portion 330 about linking member 332.

Figure 9G:
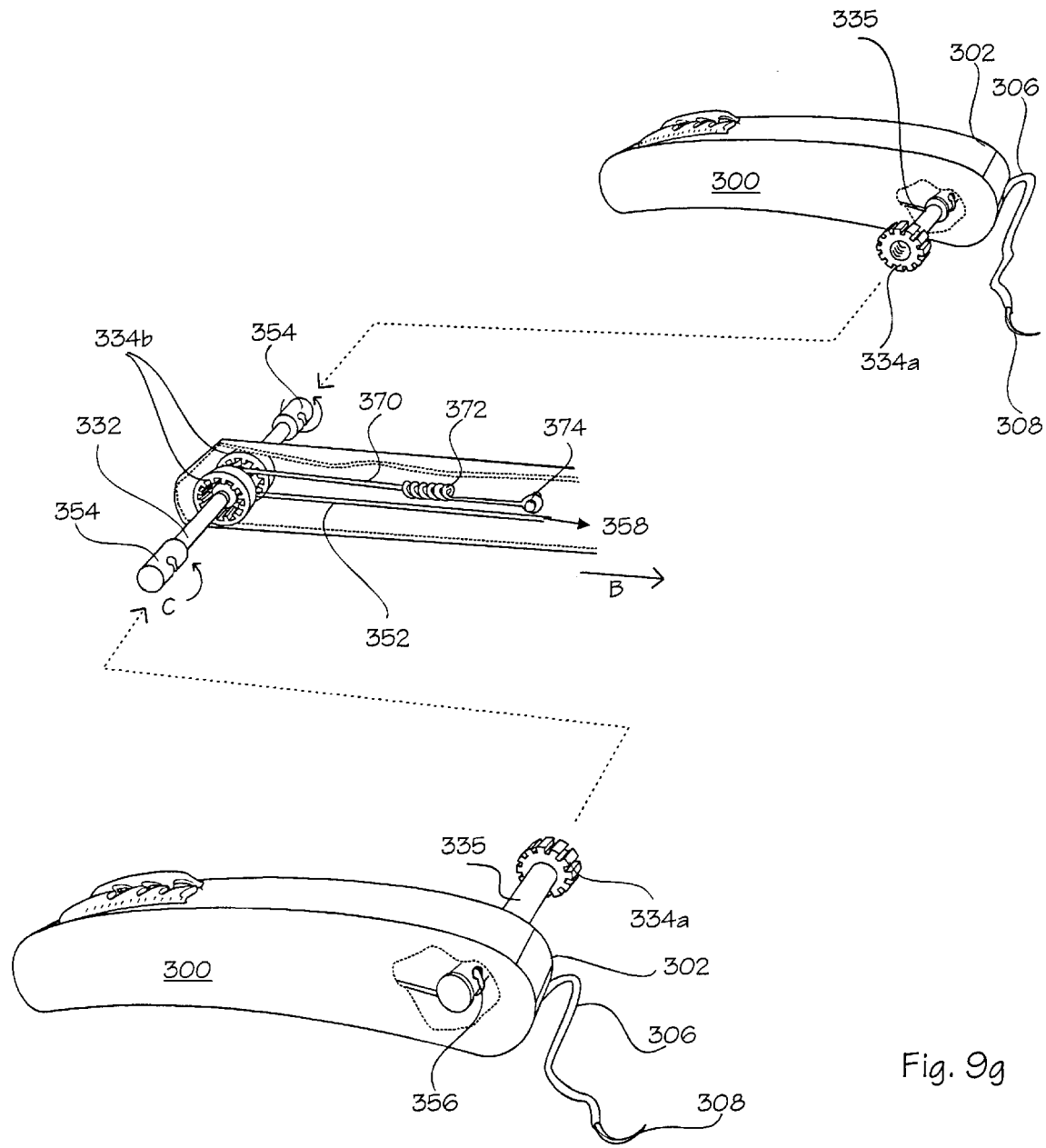
FIG. 9g is a representative exploded view of the linking member between the two stabilization pad suture controllers of the present invention.

FIG. 9g is a representative exploded view of the linking member between the two stabilization pad suture controllers of the present invention. The drawings show a suture tightening mechanism. As shown, hollow shafts 335 couple to toothed gear sections 334a and extend laterally from the first ends 302 of each stabilization pad 300. Horizontally mounted capstan ends 354 are coupled to either end of linking member 332, which in turn is coupled to toothed gear sections 334b.

Assembly of the device is accomplished by inserting the horizontally mounted capstan ends 354 on linking member 332 through the hollow shafts 335 on two stabilization pads 300, thus allowing the toothed gear sections 334a and 334b to engage with each other. Capstan ends 354 will engage the proximal ends 356 of stay sutures 306 within the first end 302 of each stabilization pad 300. It will be understood that the width of the device, i.e. the distance between the pads 300, may be adjusted and the sizes and position of the linking members 532 and hollow shafts 535 can be adjusted or adjustable. Similarly, the length of extension 330 can have essentially any operative length, or can be adjustable.

Suture control lever 350 acts on linking member 332 according to the following description. Control cable 352 is coupled to control lever 350 at a proximal end 358. Control cable extends to and wraps around linking member 332, terminating in distal end 370. In a preferred embodiment, the distal end 370 of control cable 352 is coupled to spring element 372 in turn fixed in position 374 within extension portion 330. Thus, retraction of suture control lever 350 will draw control cable 352 in direction B causing linking member 332 to rotate in direction C. Capstan ends 354 serve as winch-like winding centers for the proximal ends 356 of suture 306 such that upon rotation of linking member 332 in direction C, the suture 306 will be caused to tighten up from underneath the coronary artery 202 and cause a local, temporary occlusion of the coronary artery at the point at which the stay suture 306 passes underneath the coronary artery (not shown).

Therefore, this tightening of the stay sutures 306 in situ underneath a coronary artery 202 causes a localized upward force. As described above, a downward force of the stabilization pads 300 directly on the surface of the heart is developed by the positioning and placement of the extension member 330 in combination with a mounting device 406 (see FIG. 10). In combination, the upward forces and the downward forces developed by the device act on the heart in a compressive manner, resulting in a degree of control and stabilization heretofore unobtainable with the apparatus of the prior art.

Precise adjustment of the tension in the stay sutures 306 and suture control lever 350 is achieved with the following mechanism. (It will be understood that although the description that follows is directed to the suture control mechanism, a similar mechanism is provided in the anti-rotation mechanism.) The operative end of suture control lever 350 rotates within the handle 344 about splined pin 360, as shown in FIG. 9d. Splined pin 360 has a first head 362, a central shaft 364 and a splined portion 366 adjacent a second head 368. A correspondingly shaped opening 376 is provided in the housing of the handle 344.

Once the silastic or other material stay suture 306 has been placed underneath the coronary artery 202, and the appropriate tension set by adjustment of the suture control lever 350, the splined pin 360 can be manually moved into the handle portion 344, in direction D, shown in FIG. 9e such that the splined portion 366 engages the handle 344 and prevents rotation about pin 360. This will lock the control lever 350 into position with a given tension developed within stay suture 306. Thereafter, manually applying an opposing force on second head 368 will drive the locking pin 360 in direction E as shown in FIG. 9f, and unlock the control lever 350, allowing the tension on stay suture 306 to be released as desired.

Another feature of the configuration described herein prevents excessive force from being developed within the stay suture/stabilization pad. Excessive force applied to the suture control lever 350 will be dissipated, damped or somewhat absorbed by spring member 372 shown in FIG. 9g, thus preventing undesirable trauma to the coronary artery 202 and surrounding tissue.

It will be understood that the apparatus disclosed herein are but a few of the preferred embodiments. The stabilization pads 300 are intended to be disposable, while the handle portion 344 along with rotation control and suture control mechanisms are intended to be re-usable. It will be understood that the entire apparatus can be integral, without the need for the stabilization pads 300 to be separable from the remainder of the apparatus. Furthermore, while the preferred embodiment may have stabilization pads of between about 1 and about 2 inches long or more or less, and each about ⅛ to about ¼ wide or more or less, these dimensions can be varied.

Figure 10:
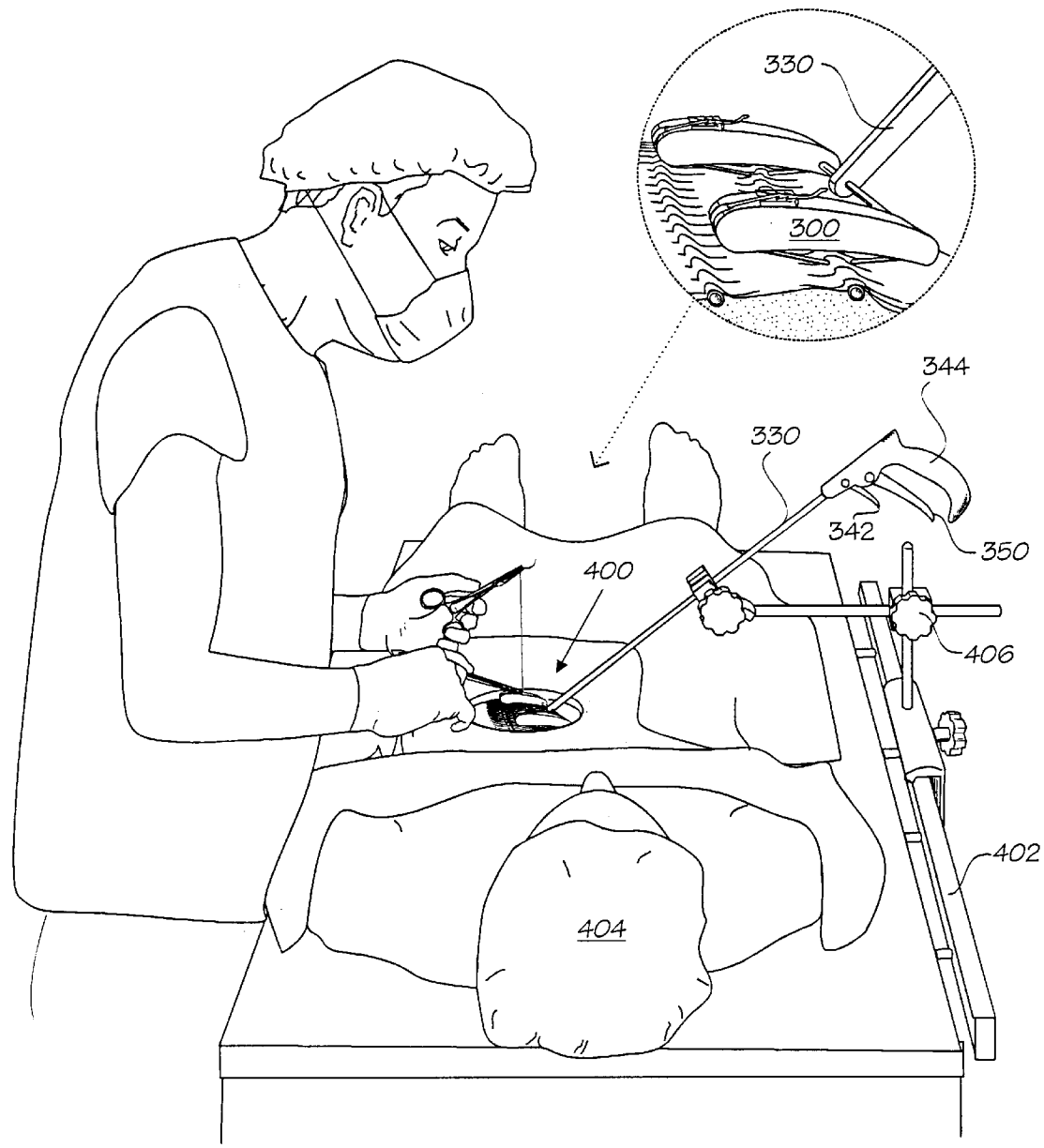
FIG. 10 is a representative view of a preferred embodiment of the present invention mounted in an operative configuration to the operating platform.

FIG. 10 is a representative view of a preferred embodiment of the heart stabilizer with controllable stay suture device 400 of the present invention mounted in an operative configuration to the operating platform 402. As will be understood by the foregoing, once an opening is created, or an exposed field otherwise made available, the apparatus can be mounted to an operating platform 402, in an operative position relative to the patient 404, using selected mounting devices 406. Such devices including sections of tubing, clamps, etc. In another configuration, the device 400 is mounted relative to the patient 404 with an adjustable, flexible, optionally telescoping, tightenable mounting arm which can be set into any position desired.

Figure 11A:
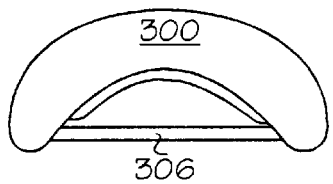
FIGS. 11a–11c are representative section and perspective view of the stabilization pad suture controller of the present invention.
Figure 11B:
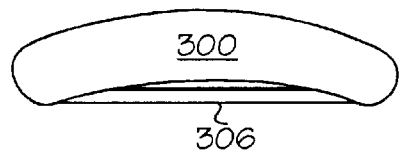
Figure 11C:
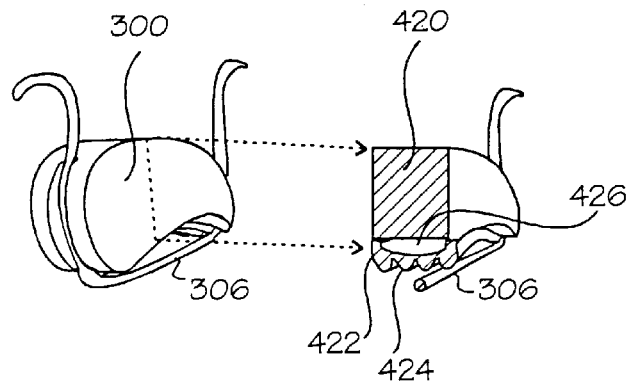

FIGS. 11a–11c are representative section and perspective view of the stabilization pad suture controller 300 of the present invention. In FIGS. 11a and 11b, the camber or degree of curvature of the pad 300 is different. The cardiac surgeon can select the optimum shape of pad 300 for the particular patient, depending upon the size and shape of the heart, the position on the heart to be accessed and isolated, the position of the coronary artery in the heart, i.e. on the top surface, somewhat submerged within myocardium, etc. In a preferred embodiment, the curvature of the stabilization pad 300 matches the to curvature of the patient's heart. By providing pads 300 with a variety of sizes and shapes, including different degrees of curvature, the cardiac surgeon can obtain the most effective occlusion and stabilization possible.

In FIG. 11c, the cross sectional face 420 of the pad 300 is shown. Along the contacting surface 422, one or more narrow ribs 424 form a sharp occluding edge to form an occlusion in a well defined, narrow area across the coronary artery. The extending rib or ribs 424 will also serve to prevent slippage between the contacting surface 422 and the surface of the heart. The contacting surface 422 is preferably formed of a soft, supple, absorbing rubber or silicone-type material. In a preferred embodiment, a pocket 426 between the contacting surface 422 and the pad 300 acts as a cushioning element and serves to enhance the atraumatic, non-damaging gripping contact surface 422.

Figure 12:
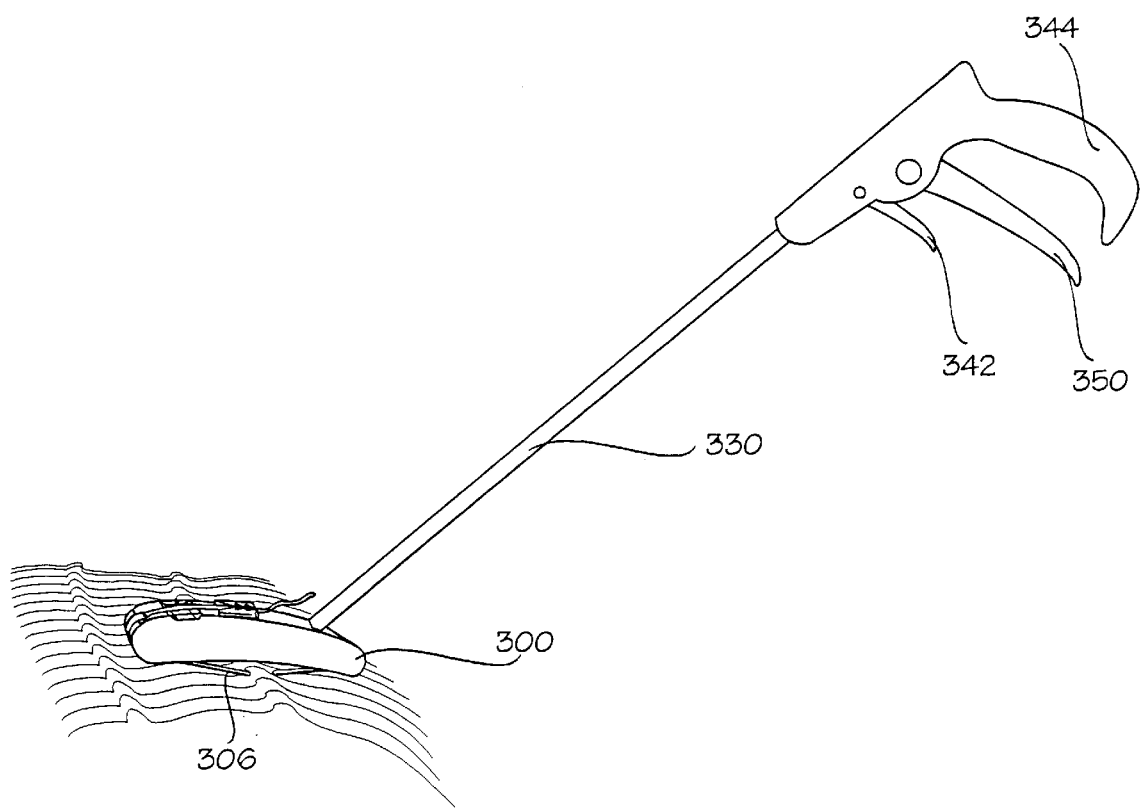
FIG. 12 is a representative perspective view of a single stabilization pad suture controller with extension and handle portions of the present invention.

FIG. 12 is a representative perspective view of a single stabilization pad suture controller with extension and handle portions of the present invention. The stabilization pad 300 is rotatably coupled, as in the prior embodiments, to extension portion 330 and handle portion 344, comprising rotation lever 342 as well as suture control lever 350. In this embodiment, the single stabilization pad 300 can be controlled individually apart from a second pad, both in regards to rotation of the pad at the distal end of the extension member 330 as well as with regard Lo control of the tension of stay suture 306 by control lever 350.

It will be understood that although FIG. 12 shows a single stabilization pad 300 device, in reality there may be backflow of blood through the coronary arteries of the heart. Therefore, in general, the preferred embodiment of the device of the present invention with two different stabilization pads will have greater utility, although there will be circumstances where the embodiment shown in FIG. 12 will be preferred. Furthermore, it will be understood that three or more stabilization pads may also be combined into a single device, as desired.

Figure 13A:
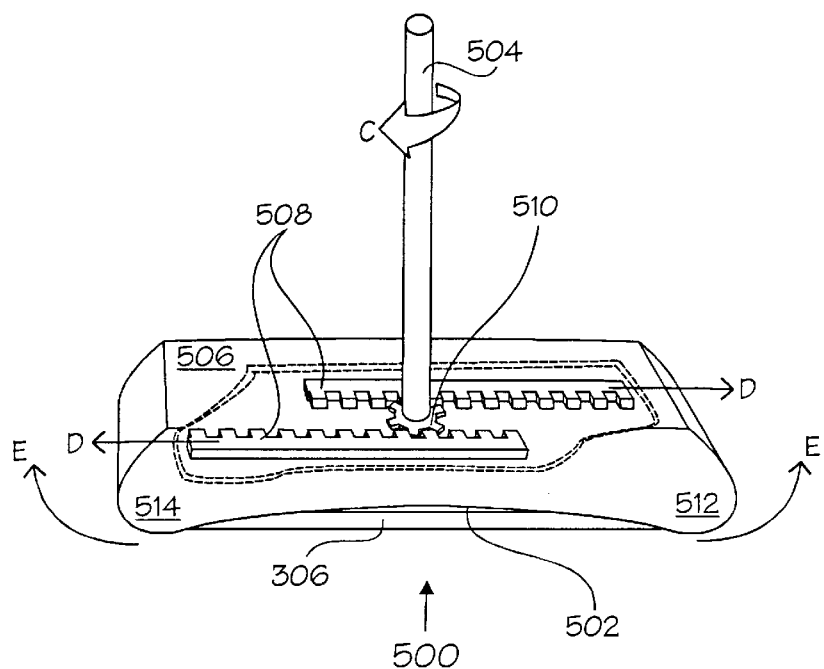
FIGS. 13a and 13b are representative perspective drawings of preferred embodiments of variable curvature stabilization pad suture controllers of the present invention.
Figure 13B:
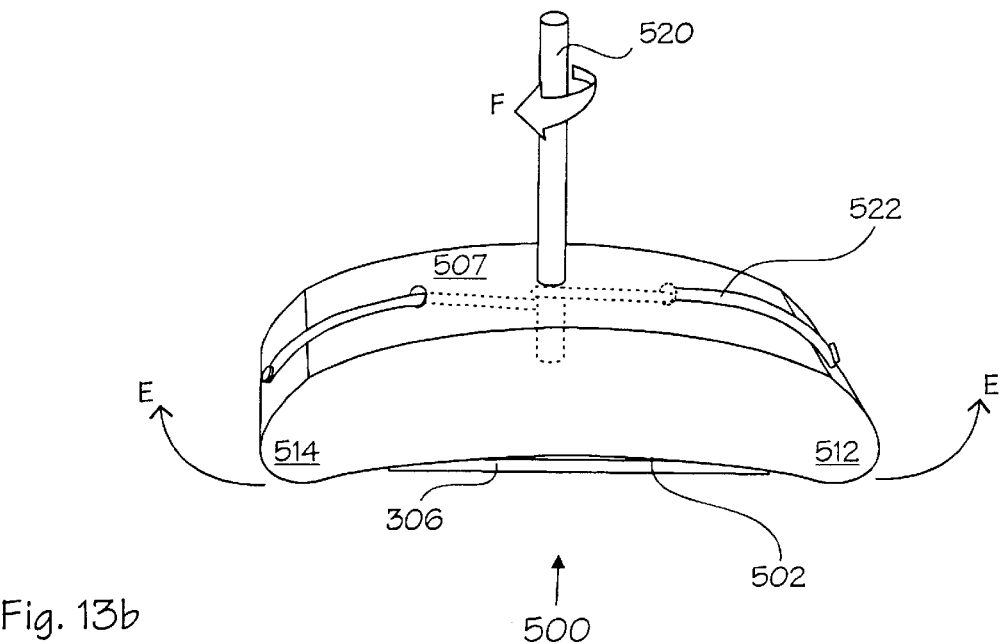

FIGS. 13a and 13b are representative perspective drawings of preferred embodiments of adjustable and/or variable curvature stabilization pad suture controllers of the present invention. In either embodiment, the stabilization pad 500 is similar to those described above, including the features of suture, suture locking means, suture cutting elements, handle means, etc. (not shown). Additionally, means for adjusting the curvature of the lower contacting surfaces 502 is included. Both of the stabilizaiton pads 500 are somewhat flexible, either by means of a hinged or bifurcated construction, construction with flexible or malleable materials such as neoprene, silicone ruber, other polymeric materials, etc., or other. In the embodiment of FIG. 13a, a rotatable shaft 504 extends from the upper portion 506 of the stabilizaiton pad 500. A set of slidable racks 508 are either on top of the pad 500, are located just under the top surface thereof or are located within the pad itself. The shaft 504 couples to the pad 500 with a gear element 510, the teeth of which engage those of the racks 508. Upon rotation of the shaft 504 and gear element 510 in direction C as shown, slidable racks D will be extended in direction D. This will lift the opposing ends 512 and 514 of the stabilization pad 500 upward in direction E, as shown. The end result is that the flexible or bifurcated stabilization pad 503 will tend to flatten out, reducing the curvature of the lower, contacting surface 502. It will be understood, therefore, that when a stay suture is placed underneath a coronary artery, and both ends of the stay suture are fixed to the stabilization pad 500, the action of flattening the lower contacting surface 502 and reducing the curvature of the stabilization pad 500 will result in drawing the stay suture up toward the contacting surface 502, thereby atraumatically pinching and occluding the coronary artery.

FIG. 13b shows a second mechanism for reducing the curvature of the lower contacting surface 502 of the stabilization pad 500. In this embodiment, a rotating shaft 520 extends upwardly from the upper surface 507 of the stabilization pad 530. Wires or cables 522 lie on top of the stabilization pad S00 or within the upper portion thereof, and are attached to either end 512 and 514 of the device. Cables 522 terminate at the rotating shaft 520 and wind around it. Therefore, upon rotation of shaft 520 in direction F as shown, the cable 522 will be tightened across the upper surface 507 and thereby lift the opposing ends 512 and 514 upwards in direction E as shown. As described relative to the embodiment shown in FIG. 13a, lifting opposing ends 512 and 514 will reduce the curvature of the lower contacting surface 502 of the stabilization pad 500, and a stay suture (not shown) threaded underneath a coronary artery and fixed to either end of the pad 500 will be drawn upwards, atraumatically pinching and occluding the coronary artery at the desired location.

The present invention is intended for use when a MIDCAB bypass surgery is done alone or with any medical laser, in particular TMR lasers (Holmium, $CO^2$ or excimer) and TMR. In TMR, the heart stabilizer of the present invention is used to lift and rotate the heart to provide access to the back normally non-exposed surface of the heart. Likewise, other catheter and/or surgical equipment and/or surgical procedures may find value in heart immobilization, stabilization and retraction, as provided by the present invention.

Additionally, as described above, TMR may follow the MIDCAB procedure in non-bypassed areas of myocardium even if bypass protection is not elected in those areas. It will also be understood that the apparatus and method of the present invention as described herein which includes the combination or use with of any conventional mechanism or method which are known to those skilled in the art, are included within the scope of this invention.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A heart stabilizer and suture control device for stabilizing the heart and for occluding a preselected portion of one or more coronary arteries, the device comprising:
   two stabilization pads, the stabilization pads each having an operative size and shape;
   a tension suture coupled to each stabilization pad, the sutures each having a distal end to be fixed in place to the stabilization pads, the sutures each also having a proximal end which can be coupled to the stabilization pads; and
   a suture controller, such that when operatively positioned adjacent one or more coronary arteries to be occluded, the tension sutures associated with each stabilization pad can be tightened or loosened to cause changes in the occlusion forces on the one or more coronary arteries as desired.

2. The device of claim 1 further comprising a linking member operatively coupling the two stabilization pads together.

3. The device of claim 2 further comprising an extension portion rotatably coupled to the inking member.

4. The device of claim 3 further comprising a rotation locking mechanism for locking the rotatable extension in a fixed position relative to the two stabilization pads.

5. The device of claim 1 in which the suture controller comprises a handle, and in which the sutures of each stabilization pad are tightened about their respective stabilization pad by means of a suture control lever coupled to the handle of the device.

6. The device of claim 1 wherein the distal end of the suture has a piercing tip.

7. The device of claim 1 wherein each pad defines an upper and lower surface, the upper surface having a lock for the distal ends of the sutures.

8. The device of claim 7 wherein the lock is a hinged shutter.

9. The device of claim 7 wherein the lock is a jam cleat.

10. The device of claim 7 wherein the lower surface further comprises at least one outwardly extending rib element.

11. The device of claim 7 wherein the lower surface is made from a material having a durometer atraumatic to tissue.

12. The device of claim 7 wherein each lower surface is contoured and generally conforming in shape to a curvature of an external surface of a heart.

13. The device of claim 12 wherein the contour of the lower surface has a predetermined shape.

14. The device of claim 13 wherein each of said pads further defines a suture cutting element.

15. A heart stabilizer and suture control device for stabilizing the heart and for occluding a preselected portion of coronary artery, the device comprising:

two stabilization pads each having a first end and a second end and a lower tissue contacting surface, the second ends each having suture retaining grooves, each pad having a suture lock;

a linking member linking the two stabilization pads at an operative distance apart;

a suture associated with each of the stabilization pads, each said suture having a proximal end coupled to the linking member and extending beneath the lower tissue contacting surface between the first end and the suture retaining groove of the second end, each the suture having a distal end which can be locked to the stabilization pads when attached to the suture lock; and a rotation mechanism operatively attached to the linking member, rotating the linking member causing the proximal end of the suture to be wound onto the linking member to tighten the suture between the first end and the second end of each stabilization pad thereby urging a coronary artery against the tissue contacting surface when the suture is threaded under the coronary artery.

16. The device of claim 15 in which the linking member is adjustable to vary a distance between the two pads and the rotation mechanism comprises a handle portion with a suture control lever coupled thereto, the handle portion adjustably attached to the linking member, a first cable extending from the linking member to the suture control lever, movement of the suture control lever translated into rotation of the linking member.

17. The device of claim 15 in which the tissue contacting surfaces of the stabilization pads each have a narrow, extending rib thereon.

18. The device of claim 15 further comprising a mounting tool for mounting the stabilizer and suture control device in a fixed position relative to the patient.

19. A vessel occlusion device particularly suited for minimally invasive surgery requiring temporary occlusion of one or more coronary arteries comprising:

at least one pad defining a body with upper and lower surfaces, the lower surface having an elongated suture with a first end attached to the pad and a second end attached to a needle, the upper surface having a suture lock and made from a material having a rigidity sufficient to allow tightening of the suture thereon to occlude an implanted or explanted coronary artery positioned between the lower surface and the suture therebeneath, the at least one pad having first and second ends, the first end attached to the suture and the second end with a suture guide;

a bar attached to the at least one pad; and a handle attached to the bar.

20. The device of claim 19 wherein the bar is rotatably attached to the pad and the handle defines a lever for adjusting the position of the bar relative to the at least one pad.

21. The device of claim 19 further comprising a locking mechanism for securing a selected position of the bar.

22. The device of claim 20 further comprising a second lever attached to the handle for tightening and loosening the suture.

23. The device of claim 19 further comprising first and second pads attached by a lateral rod, the bar connecting to the lateral rod.

24. The device of claim 19 wherein the lower surface of the at least one pad defines a cushioning surface between the upper surface and the suture.

25. The device of claim 19 wherein the lock is a hinged shutter.

26. The device of claim 19 wherein the lock is a jam cleat.

27. The device of claim 19 wherein the at least one pad further defines a suture cutting element.

28. The device of claim 19 wherein the at least one pad defines a contoured lower surface generally conforming in shape to a curvature of an external surface of a heart.

29. The device of claim 28 wherein the contoured lower surface has a predetermined shape.

30. The device of claim 28 wherein the lower surface further comprises at least one outwardly extending rib element.

31. A method for temporarily occluding blood flow through a coronary artery comprising the following steps:

(a) providing a device having at least one pad defining a body with upper and lower surfaces, the lower surface having a suture mechanism with a first end attached to the pad and a second end extendable to the upper surface, a suture controller for tightening the suture mechanism, the upper surface having a suture lock;

(b) positioning the device at the coronary artery to be occluded;

(c) threading the second end of the suture mechanism underneath the coronary artery;

(d) applying a first, essentially downward force on the pad; and (e) operating the suture controller to cause the suture to apply a second, opposing force in an upward direction from beneath the coronary artery.

32. The method of claim 31 in which step (c) further comprises extending the second end to the upper surface and securing said second end thereto in the suture lock.

33. The method of claim 31 in which the device has two pads and further includes a linking member positioned between and connected to each of the two pads, the device further including a bar adjustably connected to the linking member and to a handle, the suture controller attached to the handle and having a cable connected to the linking member, the suture controller rotating the linking member to tighten the suture mechanism, wherein said step (d) of the method further comprising positioning the adjustable bar to apply the downward pressure, and said step (e) further comprising rotating the linking member to tighten the suture.

* * * * *